United States Patent [19]

Sudo

[11] Patent Number: 5,637,100
[45] Date of Patent: Jun. 10, 1997

[54] SYRINGE-CUM-CONTAINER

[75] Inventor: Morihiro Sudo, Tokyo, Japan

[73] Assignee: Daikyo Seiko, Ltd., Tokyo, Japan

[21] Appl. No.: 538,379

[22] Filed: Oct. 3, 1995

Related U.S. Application Data

[63] Continuation of Ser. No. 155,201, Nov. 22, 1993, abandoned.

[30] Foreign Application Priority Data

Aug. 27, 1993 [JP] Japan .................. 5-212949
Nov. 27, 1993 [JP] Japan .................. 5-318583

[51] Int. Cl.$^6$ .................................... A61M 5/315
[52] U.S. Cl. ..................... 604/238; 604/89; 604/218
[58] Field of Search ........................ 604/82, 89, 90, 604/92, 191, 218, 238, 181, 187

[56] References Cited

U.S. PATENT DOCUMENTS

| | | | |
|---|---|---|---|
| 1,308,919 | 7/1919 | Sellar | 604/238 |
| 1,316,394 | 9/1919 | Sellar | 604/238 |
| 2,238,582 | 4/1941 | Dickinson et al. | 604/238 |
| 2,591,046 | 4/1952 | Brown | 604/90 |
| 2,798,487 | 7/1957 | Ferguson | 604/238 |
| 2,893,390 | 7/1959 | Lockhart | 604/238 |
| 4,235,235 | 11/1980 | Bekkering | 604/238 |
| 4,469,482 | 9/1984 | Lissenburg et al. | 604/238 |
| 4,496,344 | 1/1985 | Kamstra | 604/90 |
| 4,613,326 | 9/1986 | Szware | 604/238 |
| 4,668,223 | 5/1987 | Grotenhuis | 604/191 |
| 4,792,329 | 12/1988 | Shreuder | 604/191 |
| 4,952,208 | 8/1990 | Lix | 604/218 |
| 5,282,822 | 2/1994 | Macors et al. | 604/187 |

FOREIGN PATENT DOCUMENTS

| | | | |
|---|---|---|---|
| 0302248 | 2/1989 | European Pat. Off. . | |
| 705392 | 3/1954 | United Kingdom . | |
| 9201485 | 2/1992 | WIPO | 604/191 |

*Primary Examiner*—Vincent Millin
*Assistant Examiner*—N. Kent Gring
*Attorney, Agent, or Firm*—Wenderoth, Lind & Ponack

[57] ABSTRACT

An improved syringe is provided which can be used in any step of preparation of a medicament by vacuum freeze-drying, etc., storage of a medicament, mixing of medicaments and dosing of a medicament in a sanitary and stable manner. The syringe comprises a cylinder having a front end part at one end and an opening part at another end and a bypass running in the longitudinal direction near the central position of the cylinder on the inner wall within the cylinder. A first sealing stopper is adapted, at a position toward the opening part of the cylinder from the bypass within the cylinder, to form a first compartment between the front end of the cylinder and the first sealing stopper. A second sealing is stopper adapted, at a position toward the opening part of the cylinder from the first sealing stopper within the cylinder, to form a second compartment between the first sealing stopper and second sealing stopper. One or more bypasses are provided in a concave form on the inner wall surface of the cylinder, and the outer circumference of the cylinder has a smooth cylindrical shape. Further one or more bypasses can be provided in a concave form in two stages on the inner wall surface of the cylinder.

15 Claims, 10 Drawing Sheets

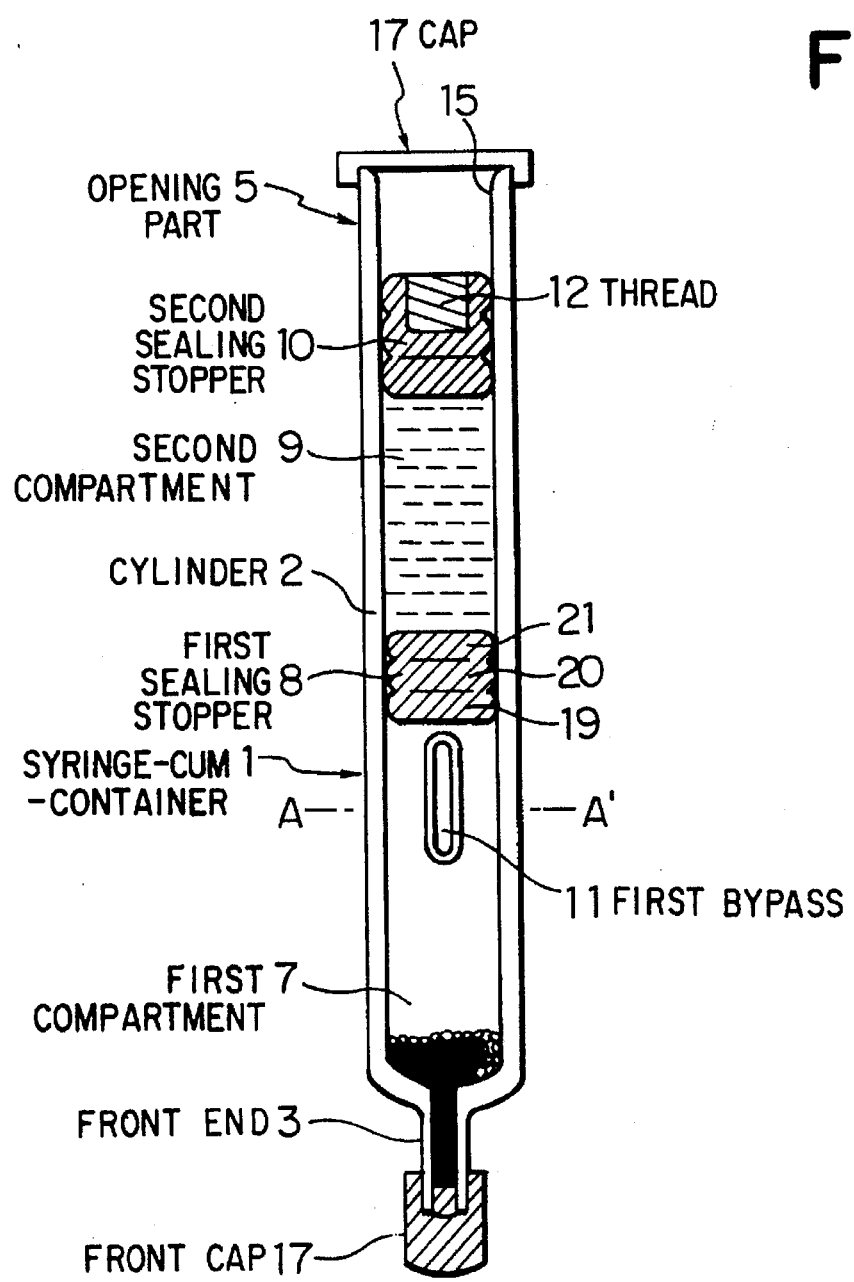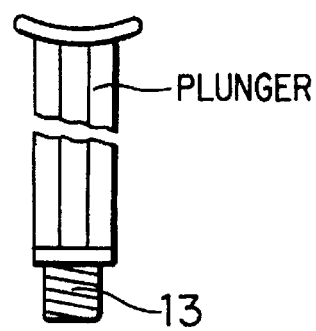

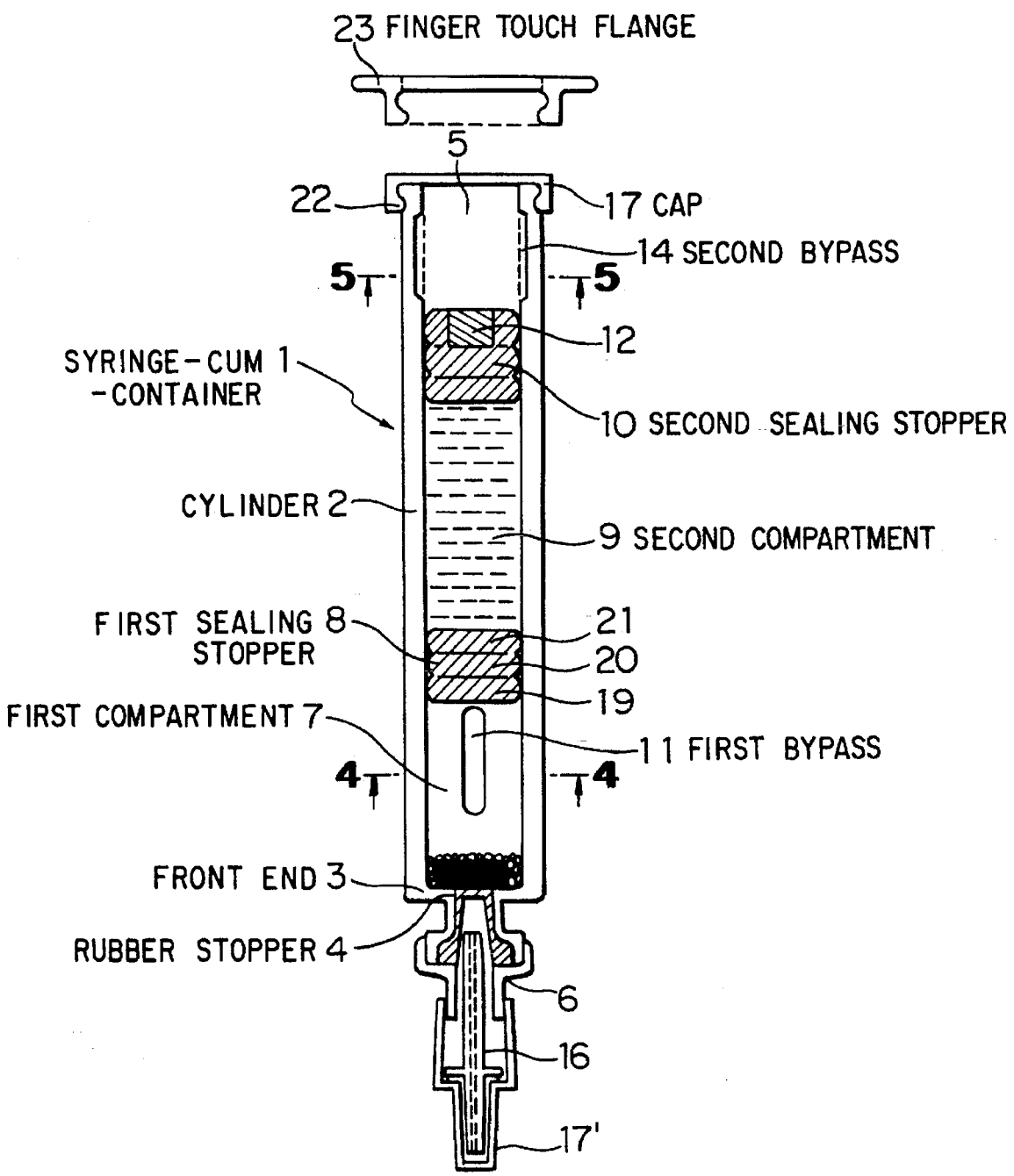

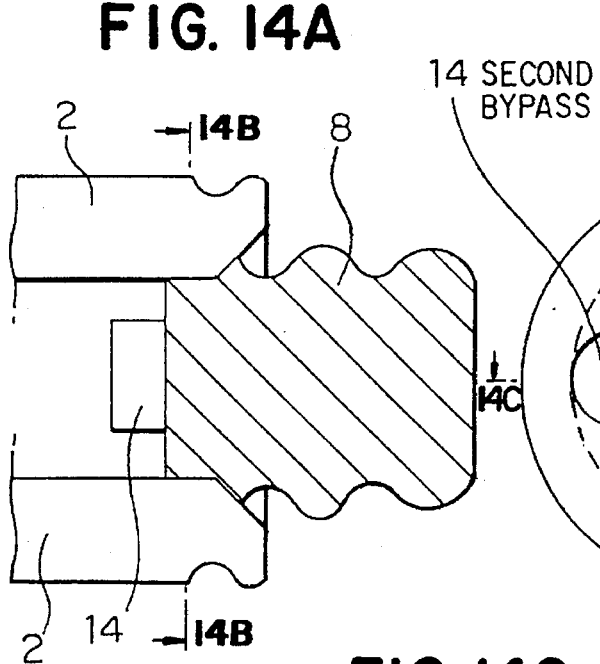
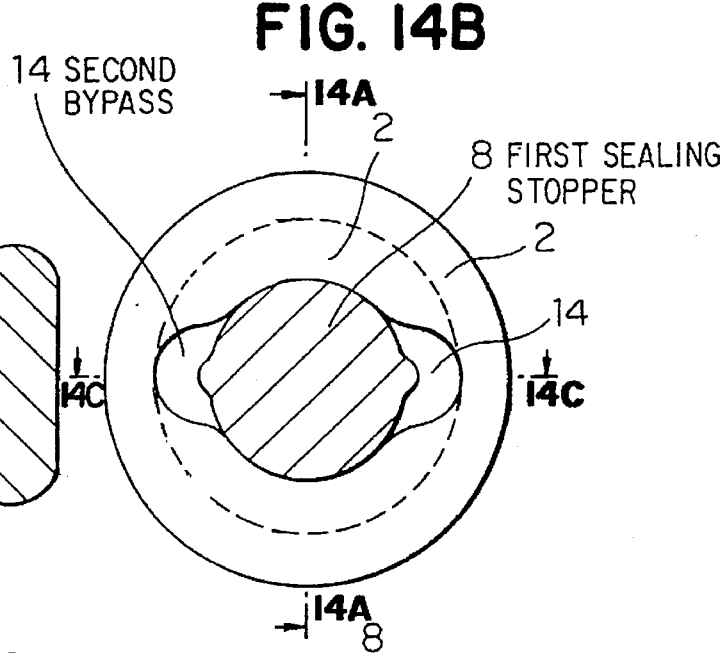
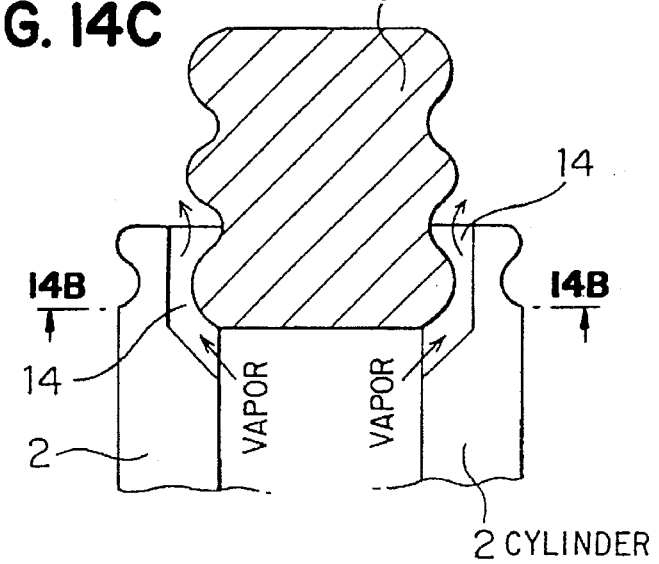

SYRINGE-CUM-CONTAINER

This application is a continuation of now abandoned application Ser. No. 08/155,201, filed on Nov. 22, 1993, now abandoned.

BACKGROUND OF THE INVENTION

1. Field of the Invention

This invention relates to a two compartment type syringe for dosing the human body with a liquid medicament or nutrient and more particularly, it is concerned with an improved syringe comprising two separated compartments each holding a medicament component and capable of rapidly mixing the medicaments during dosing and carrying out very sanitary dosing.

2. Description of the Prior Art

A syringe capable of previously filling a container with a liquid medicament or nutrient, storing it and using the container itself as an injector in a simple manner has been well known as disclosed in Japanese Utility Model Laid-Open Publication Nos. 79539/1982 and 2343/1984, Japanese Patent Laid-Open Publication Nos. 76390/1973, 16489/1973, 149894/1977, 120166/1984, 501193/1985, 502099/1986, 502086/1989 and Japanese Patent Publication No. 25389/187.

In addition, examples of injectors wherein two kinds of medicaments, for example, a medicament and a solvent, or a liquid medicament and another liquid medicament are stored and mixed or dissolved during dosing have been disclosed in Japanese Patent Laid-Open Publication Nos. 11691/1976, 22391/1977, 61755/1983, 212453/1983, 155264/1984, 72561/1985, 48377/1986, 5357/1987, 5973/1990, 82476/1981 and 96762/1982, Japanese Utility Model Publication Nos. 14465/1974 and 22315/1979 and Japanese Utility Model Laid-Open Publication Nos. 58446/1990 and 29145/1991.

An example of a two compartment type syringe of the prior art is shown in FIG. 15 and FIG. 16, in which two compartments are partitioned by a first sealing stopper 33 and medicaments stored in the two compartments can be mixed when dosing. That is, one end of a cylinder 29 comprises an open end 31, provided with, at the circumference thereof, a finger touching flange 32. The other end 30 is narrowed and sealed by a rubber stopper 38. The first sealing stopper 33 and a second sealing stopper 34 are disposed within the cylinder 29 to be in intimate frictional contact with the inner wall of the cylinder to partition the cylinder into a first compartment 35 and second compartment 36, where a powder medicament 30 is held in the first compartment 35 and distilled water is held in the second compartment in an example as shown in the Figure. Nearly at the central part but toward the narrowed end of the cylinder 29, a bypass part 37 is provided. When dissolving and mixing medicaments, the second sealing stopper 34 is moved by a plunger (not shown) toward the narrowed end and the first sealing stopper 33 is thus moved via distilled water to a position of the bypass part 37 at the narrowed end, as shown by a chain line in FIG. 15, whereby the distilled water in the second compartment 36 flows into the first compartment 35 and mixes with the powder medicament 30 in the first compartment 35 to dissolve the medicament in the distilled water and to prepare a liquid medicament. As shown in FIG. 16, the cross section at the bypass part is designed in such a shape that the outer circumference and inner wall of the cylinder are projected outward with the same thickness at the bypass part.

The prior art, as described above, aimed at mainly improving means for mixing two medicaments in a syringe and had no consideration of a problem of preparing a medicament in a container with a same shape. That is, the syringe having the shape as shown in FIG. 15 and FIG. 16 has the disadvantages that a large volume is required as a space for storage of the container in the process of preparing a medicament, etc. and the workability in adapting the first sealing stopper after filling the powder medicament and adapting the second sealing stopper after filling the second compartment with distilled water is not good, thus resulting in a sanitary problem.

SUMMARY OF THE INVENTION

It is an object of the present invention to provide an improved syringe comprising two separated compartments each holding a medicament component and capable of rapidly mixing the medicaments during dosing and carrying out very sanitary dosing.

It is another object of the present invention to provide an improved structure of a syringe which can be operated in such a manner that medicaments are held in one container in each of steps of preparing, storing, mixing and dosing the medicaments and which can be used in a sanitary and stable manner in all of the steps of preparing, storing and dosing the medicaments.

It is a further object of the present invention to provide an improved syringe which is suitable for the preparation, storage and dosing of unstable medicaments such as antibiotics, enzymes, vitamins, blood serums, vaccines, etc.

These objects can be attained by a two compartment type syringe comprising a cylinder having a front end part at one end and an opening part (open end) at another end and a bypass running in the longitudinal direction near the central position of the cylinder on the inner wall within the cylinder, a first sealing stopper adapted, at a position toward the opening part of the cylinder from the bypass within the cylinder, to form a first compartment between the front end of the cylinder and the first sealing stopper and a second sealing stopper adapted, at a position toward the opening part of the cylinder from the first sealing stopper within the cylinder, to form a second compartment between the first sealing stopper and second sealing stopper, characterized in that one or more by passes are provided in a concave form on the inner wall surface of the cylinder and the outer circumference of the cylinder has a smooth cylindrical shape.

BRIEF DESCRIPTION OF THE DRAWINGS

The accompanying drawings are to illustrate the principles and merits of the present invention in detail.

FIG. 1 is a schematic cross-sectional view of one embodiment of a syringe according to the present invention.

FIG. 2 is a schematic view of a plunger.

FIG. 3 is a schematic cross-sectional view of another embodiment of a syringe according to the present invention.

FIG. 4 is a cross-sectional view of a first bypass part along 4—4 in FIG. 3 or FIG. 6.

FIGS. 14A, B and C are cross-sectional and partially cross-sectional views of a further embodiment of the syringe according to the present invention, in which a shorter second bypass is provided.

DETAILED DESCRIPTION OF THE INVENTION

Figure 5:
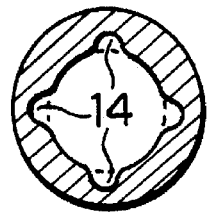
FIG. 5 is a cross-sectional view of a second bypass part along 5—5 in FIG. 3 or FIG. 6.

The inventors have made various studies on syringes to overcome the disadvantages of the prior art and consequently, have found that this object can be achieved by providing one or more bypass parts without changing the outer shape of the barrel.

Accordingly, the present invention provides a two compartment type syringe comprising a cylinder having a front end part at one end and opening part at another end and a bypass running in the longitudinal direction near the central position of the cylinder on the inner wall within the cylinder, a first sealing stopper adapted, at a position toward the opening part of the cylinder from the bypass within the cylinder, to form a first compartment between the front end of the cylinder and the first sealing stopper and a second sealing stopper adapted, at a position toward the opening part of the cylinder from the first sealing stopper within the cylinder, to form a second compartment between the first sealing stopper and second sealing stopper, characterized in that one or more bypasses are provided in the number of one or more in a concave form on the inner wall surface of the cylinder and the outer circumference of the cylinder has a smooth cylindrical shape.

Furthermore, the present invention provides a two compartment type syringe comprising a cylinder having a front end part at one end and an opening part at another end, a first bypass running in the longitudinal direction near the central position of the cylinder on the inner wall within the cylinder and a second bypass with a length longer than the thickness of a first sealing stopper or a length of ⅓ to 1 times of the thickness of a first sealing stopper, running in the longitudinal direction at a position toward the opening part from the first sealing stopper on the inner wall within the cylinder, the first sealing stopper adapted, at a position toward the opening part of the cylinder from the first bypass within the cylinder, to form a first compartment between the front end of the cylinder and the first sealing stopper and a second sealing stopper adapted, at a position toward the central part of the cylinder, to form a second compartment between the second sealing stopper and the first sealing stopper, characterized in that one or more of each of the first bypass and second bypass are provided in a concave groove form on the inner wall surface of the cylinder and the outer circumference of the cylinder has an unevenness-free cylindrical shape.

For the purpose of drying or freeze-drying in vacuum a medicament filled in a container and then rapidly sealing in a room in a process for preparing a medicament, or rendering a container suitable for storage of a medicament, mixing medicaments or dosing a medicament, the syringe of the present invention is preferably designed so that (1) the thickness of the above described first sealing stopper in the longitudinal direction (cylinder-axial direction) is less than the length of the first bypass, (2) the surface of the above described first sealing stopper and/or second sealing stopper is laminated with a resin film, or (3) the front end of the above described cylinder is formed inside in a circular bottom and sealed by a rubber stopper to form a flat surface, the rubber stopper being provided with a double-headed needle fixed. When the thickness of the wall at the opening part of the cylinder is less than that of the interior part of the cylinder, thrusting of a sealing stopper into the opening part can more readily be carried out.

The structure, function and other features of the syringe of the present invention will now be illustrated by the following examples.

FIG. 1 is a schematic cross-sectional view of one embodiment of a syringe according to the present invention, in which a bypass groove 11 (hereinafter referred to as "first bypass") running in the longitudinal direction is provided on the inner wall toward the front end from the central part of an injection cylinder 2 (hereinafter referred to as "cylinder") of a syringe 1 and a first sealing stopper 8 with a smaller length than that of the first bypass 11 is positioned toward a cylinder opening part 5 of the cylinder 2 from the first bypass 11 to form a first compartment 7 between the first sealing stopper 8 and cylinder front end part. At a position toward the cylinder opening part 5 from the first sealing stopper 8 within the cylinder, a second sealing stopper 10 is adapted to form a second compartment 9 between the first sealing stopper 8 and second sealing stopper 10, thus obtaining a cylindrical container consisting of two compartments. The first sealing stopper 8 and second sealing stopper 10 each consist of an elastic body having a plurality of annular projections on the outer circumference thereof, for example, three annular projections 19, 20 and 21. The outer diameter of the projection is rendered somewhat larger than the inner diameter of the cylinder so that, when inserted into the cylinder, the projections are intimately contacted with the inner surface of the cylinder to seal the compartment and the stopper can frictionally be moved within the cylinder. To this end, the surface of the first sealing stopper 8 or second sealing stopper 10 can be laminated with a resin film. In addition, the second sealing stopper 10 can be provided with a spiral thread 12 toward the opening part of the cylinder, which is so designed that the thread 12 can be adapted to engage a spiral projection 13 at the end of a plunger shown in FIG. 2.

An end part 15 of the upper opening part 5 of the cylinder 2 is so designed that the inner diameter of the cylinder is increased toward the opening part to be tapered and the first sealing stopper 8 or second sealing stopper 10 can readily be inserted into the cylinder. A second bypass 14 is provided in the end part with a larger diameter inside the cylinder.

Figure 6:
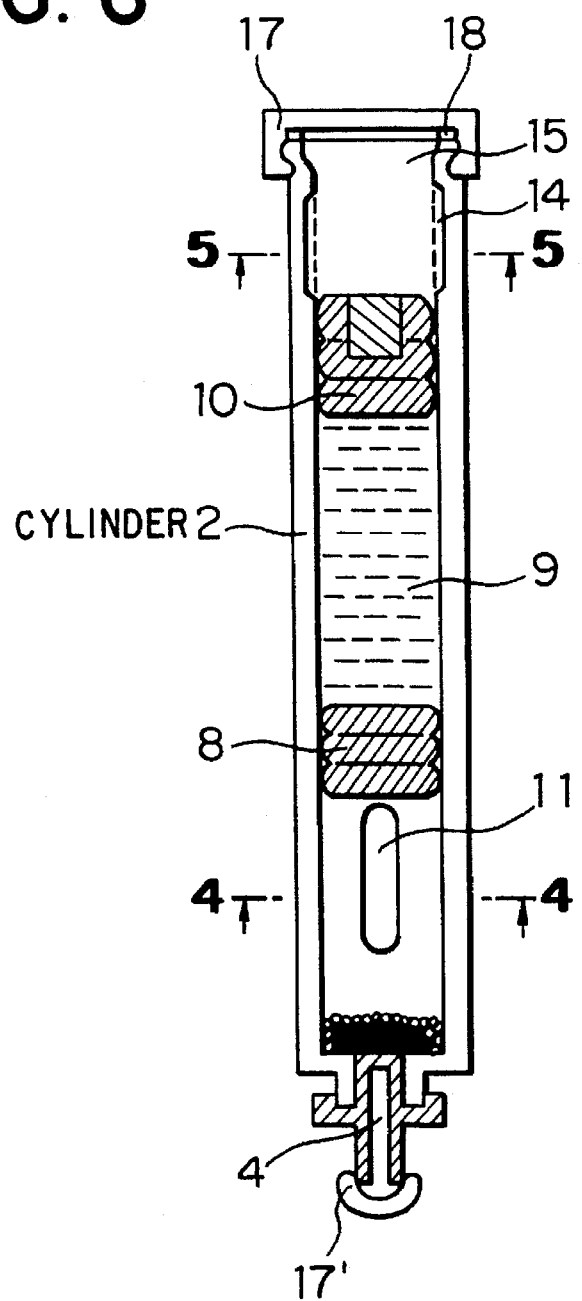
FIG. 6 is a schematic cross-sectional view of a further embodiment of a syringe according to the present invention.
Figure 12:
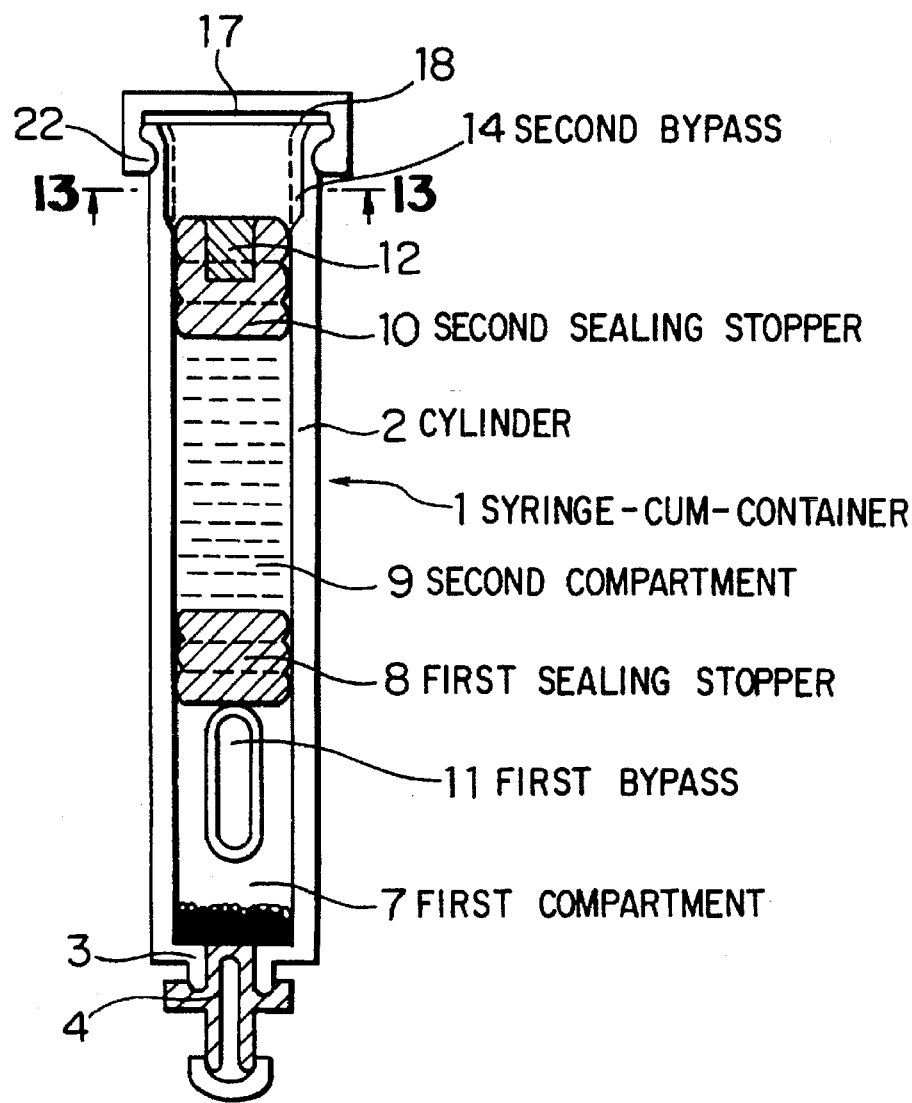
FIG. 12 is a schematic cross-sectional view of a further embodiment of a syringe according to the present invention, to illustrate an example in which a second bypass with a length that shown in about ½ of FIG. 8 is provided.
Figure 13:
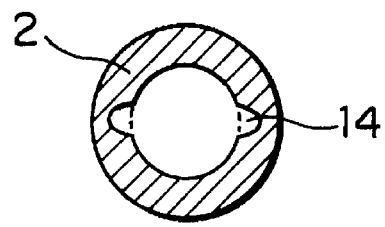
FIG. 13 is a cross-sectional view of the second bypass part along 13—13 in FIG. 12.
Figure 15:
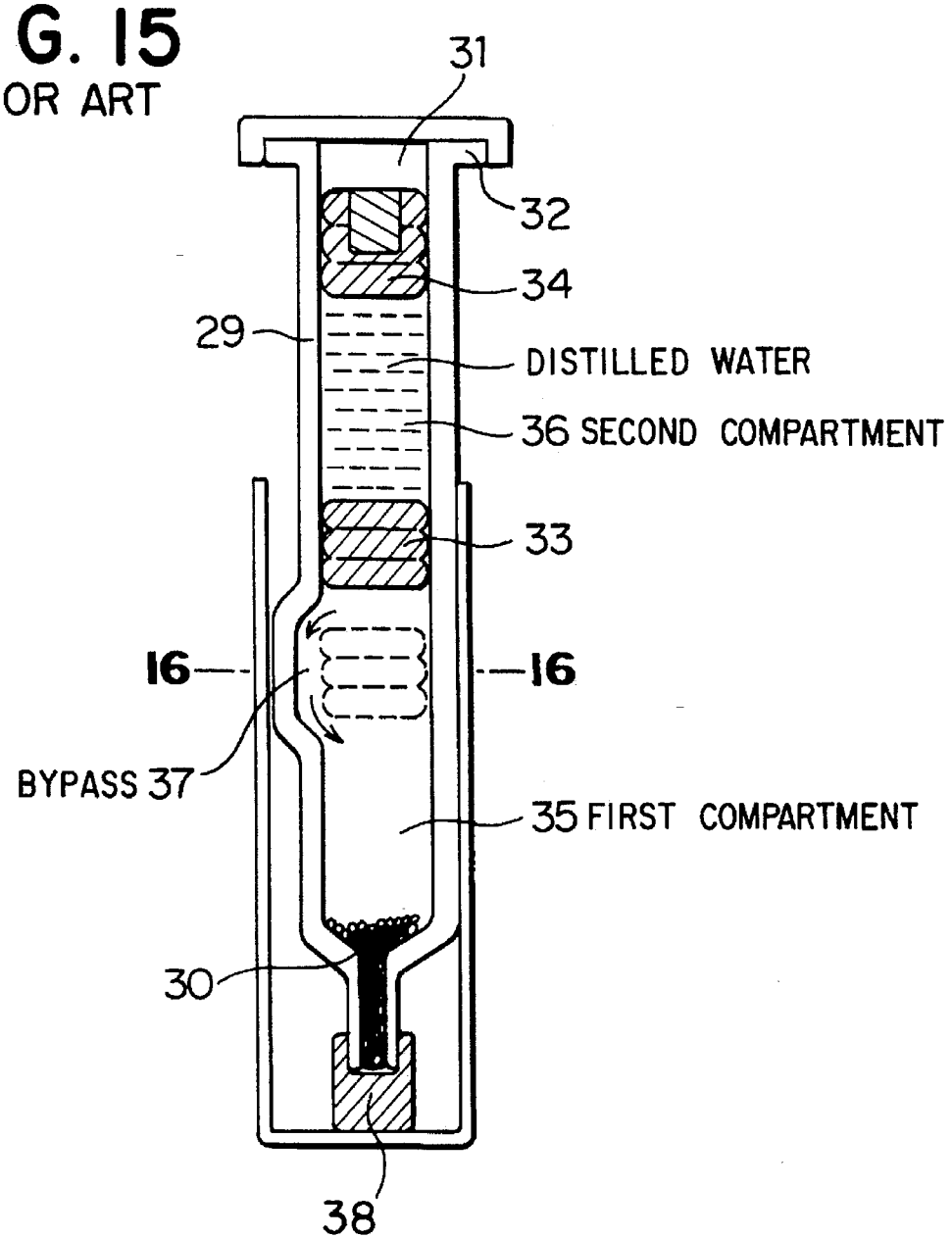
FIG. 15 is a schematic cross-sectional view of a two compartment type syringe type of the prior art, in which a bypass is provided to be projected outside the injection cylinder.
Figure 16:
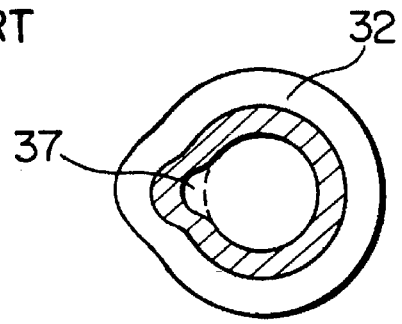
FIG. 16 is a cross-sectional view of the syringe along 16—16 in FIG. 15.

FIG. 3, FIG. 6 and FIG. 12 are schematic views to illustrate other embodiments of the present invention, in which the second bypass (or bypasses) 14 of the cylinder 2 is provided as shown in cross-section in FIG. 5 or FIG. 13. The number of the second bypass grooves is preferably 2 to 8, while that of the first bypass grooves 11 is preferably 1 to 4 as shown in cross-section in FIG. 4. As shown in the foregoing figures, the features of the present invention consist in that (1) one or more concave grooves are provided on the inner wall surface within the cylinder without providing convex forms on the outer surface of the cylinder, (2) the concave grooves are arranged in two stages of a first bypass and second bypass and (3) the length of the second bypass is $\frac{1}{3}$ to 1 times of or longer than the thickness of the first sealing stopper.

Figure 7:
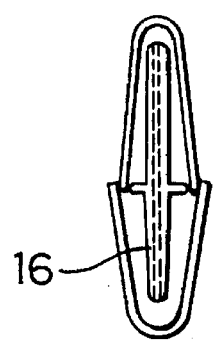
FIG. 7 is a cross-sectional view of a double-headed needle fitted to a syringe according to the present invention shown in FIG. 6.

In the present invention, the inside of a front end 3 of the cylinder 2 is provided with a reverse-U type rubber stopper 4 (i.e. a rubber stopper with a U-shape in longitudinal cross section, such that the rubber stopper has a cup-like recess therein) for sealing, as shown in FIG. 3, which has a shape such that the inner bottom of the front end 3 of the cylinder 2 forms a flat surface, is fitted to be fixed with a double-headed needle 16 by a needle fitting tube 6 and is to be penetrated by an inner needle point of the double-headed needle 16 at the center of the reverse-U type rubber stopper 4. This is a particularly preferable embodiment. FIG. 6 and FIG. 7 also show other embodiments of the present invention, in which a double-headed needle 16 and reverse-U type rubber stopper are fitted to a front end.

In the structure of the syringe of the present invention, as shown in FIG. 3, FIG. 6 and FIG. 12, there are the foregoing first compartment 7 holding a concentrated medicament or dry powdered medicament and the second compartment 9 filled with distilled water for injection or a dilute liquid medicament, both the compartments being partitioned by the first sealing stopper 8, and the cylinder 2 is sealed by the second sealing stopper 10 and rubber stopper 4 for the storage of two kinds of the medicaments. The opening part or double-headed needle is enclosed by a cap 17 or 17' and can be subjected to sterilization by ethylene gas or γ-ray to result in a very sanitary syringe.

As shown in FIG. 3, the opening part of the cylinder can be provided with a finger (or finger-engaging flange) touching flange 23. The flange 23 is engaged with a peripheral concave part 22 of the opening part and thus fixed. This device is a fitting, used for handling by fingers when dosing an injection medicament or moving a plunger and is not used in a process for the preparation of a medicament (filling, freeze-drying), during which the cylinder can maintain a simple outer shape of a cylinder.

Figure 8:
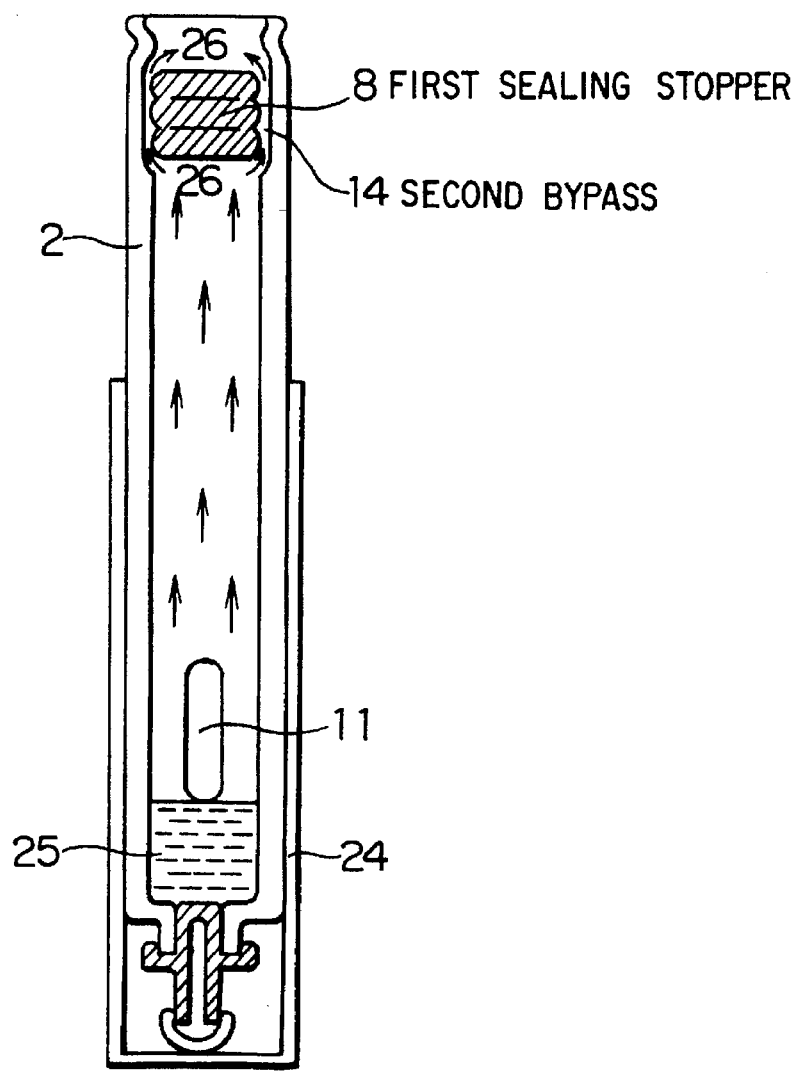
FIG. 8 is a schematic cross-sectional view to illustrate preparation of a medicament by concentrating a liquid medicament with a low concentration using a syringe according to the present invention.
Figure 9:
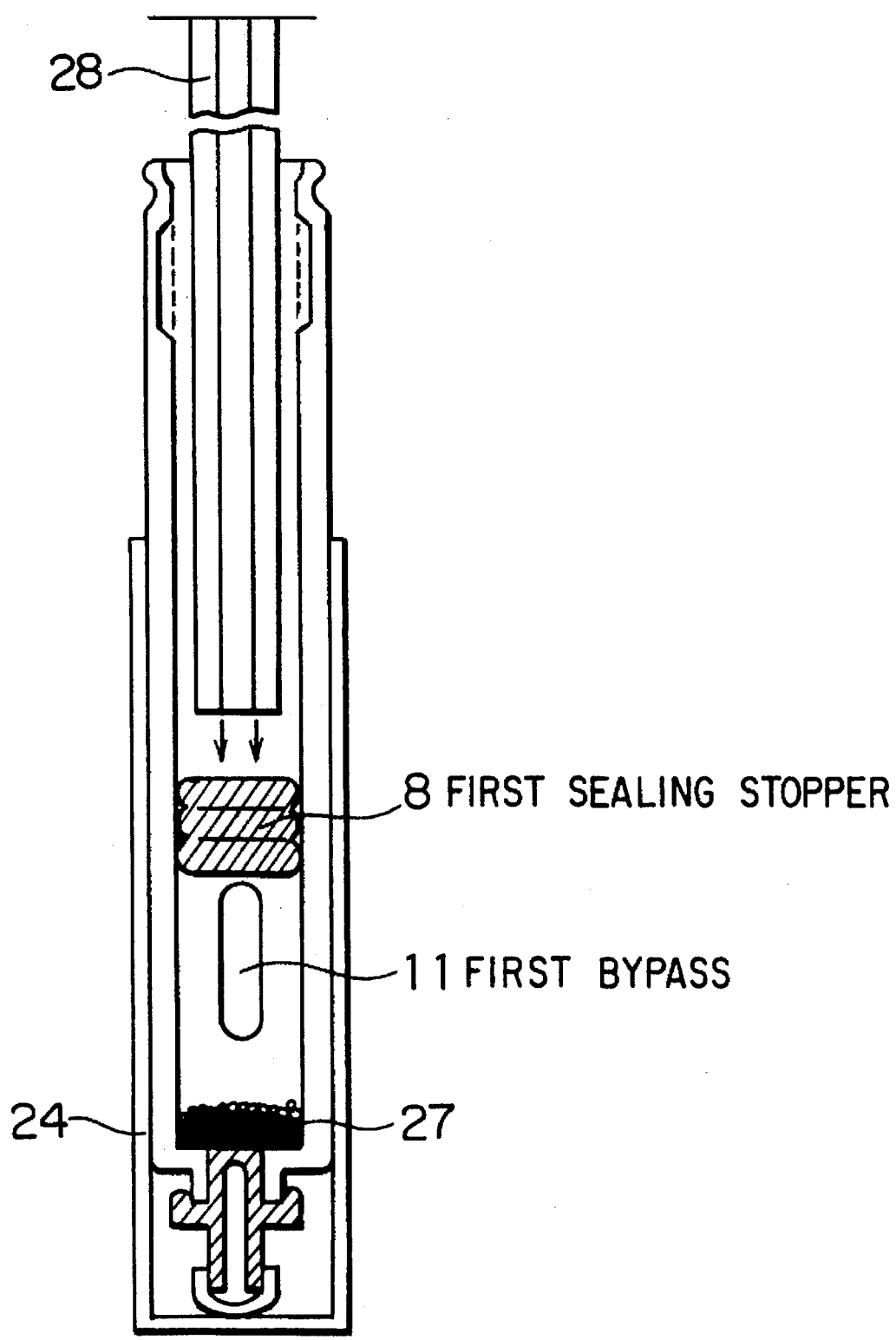
FIG. 9 is a schematic cross-sectional view showing forced adaptation of the first sealing stopper in the cylinder following the step of FIG. 8, using a syringe according to the present invention.

FIG. 8 and FIG. 9 show that the syringe of the present invention has a structure suitable for the preparation of a medicament, i.e. concentration of a dilute liquid medicament, in particular, freeze-drying in vacuum of a medicament. The front end 3 of the cylinder 2 is sealed by the rubber stopper 4, and a suitable quantity of a dilute liquid medicament 25 as a raw material for the medicament is charged and dried in a sterilized drying chamber (which can be evacuated or supplied with sterilizable air). For the preparation of an unstable medicament, i.e. a medicament readily affected by heat or oxygen such as antibiotics, enzymes, vitamins, etc., in particular, a raw liquor is subjected to freeze-drying in vacuum, for example, at a temperature of $-10°$ C. to $-60°$ C. using liquid nitrogen and a vacuum degree of $10^{-3}$ to 10 Torr. The above described structure is suitable for the concentration and drying of a medicament under such very severer conditions.

In the present invention, the length of the second bypass can be rendered shorter than the thickness of the first sealing stopper and $\frac{1}{3}$ to 1 times, preferably $\frac{1}{2}$ to 1 times as large as the thickness of the first sealing stopper. In FIG. 12, the cylinder 2 has a second bypass with a length of about $\frac{1}{2}$ of that of the second bypass in FIG. 8, but the first sealing stopper is fixed to the inner wall of the cylinder in FIG. 12 and a vapor 26 to be dried can pass through the bypass 14 and can be evaporated as in the case of FIG. 8.

FIG. 13 shows a cross-section of FIG. 12. FIG. 14 shows a cross-sectional view along a plane vertical to the central axis of the cylinder and a partial cross-sectional views in the cylinder-axial direction, in an example wherein the length of the second bypass is rendered somewhat longer than about $\frac{1}{3}$ of the thickness of the first sealing stopper. The second bypass is shorter, but is adequately fixed to the inner wall of the cylinder and a vapor can be discharged through the second bypass groove during concentrating and drying of a medicament. In this example, the vapor discharge path is so short that the apparatus can be small-sized and is free from reprecipitation of the vapor. If the length of the bypass is shorter than $\frac{1}{3}$ of the first sealing stopper, however, it is difficult to thrust forcibly the first sealing stopper into the second bypass in a drying chamber and to hold the sealing stopper on the inner wall of the cylinder in stable manner during drying.

The reasons why the syringe of the present invention is suitable for the above described conditions are as follows:

(1) Since the outer shape of the cylinder 2 is circular and the first bypass and second bypass are provided respectively in the form of a concave groove on the inner wall, a cooling medium, i.e. liquid nitrogen flows well during processing in a freeze-drying chamber and the cylinders each having a circular outer shape can adjacently be arranged to be contacted with each other by a net-shaped fixing means, thus maximizing the number of processing containers per unit area and charging a larger number of the processing containers in the drying chamber as compared with those of the prior art having bypass parts projecting outside the cylinders. Furthermore, the syringe of the present invention is also advantageous from an economical point of view, i.e. installation costs, production unit costs, etc.

(2) Position and Shape of Second Bypass

Since the second bypass and opening part of the cylinder 2 are adjacently arranged as shown in FIG. 8, a large number of grooves, i.e. 2 to 8 grooves are provided with large areas, and when an annular, thick first sealing stopper is inserted in the bypasses, the vapor 26 of the medicament 25 to be concentrated is passed through the second bypasses 14 during drying with an effect similar to a distillation column. In the case of providing a second bypass with a shorter length than the first sealing stopper, the installation cost can be reduced and reprecipitation can be prevented because of the shorter vapor path.

(3) The front end 3 of the cylinder 2 is formed to give a round bottom and a hole for an injection needle is enclosed by a reverse-U type rubber stopper in such a manner that unevenness is reduced to as little as possible.

(4) When a liquid medicament in the cylinder 2 is fully concentrated and dried to be a powdered medicament, the first sealing stopper 8 is operated by a thrusting means 28 and inserted in the central part of the cylinder 2 and above the first bypass 11 in the drying chamber, as shown in FIG. 9, thus tightly enclosing a dried powder.

According to the above described four items, an injection medicament can be enclosed in the cylinder 2 by the first sealing stopper in a drying chamber, in particular, in a vacuum freeze-drying and sterilizing chamber. The conditions required for such a process for the preparation of a medicament can thus be adequately satisfied.

Of a number of medicaments, a powder medicament stable in the air and sterilizable by heating can be charged in the syringe of the present invention having only the first bypass in the cylinder 2 in a mere sterilizing chamber, that is, by charging the concentrated powder medicament in the first compartment and a diluted medicament or distilled water for injection in the second compartment.

In the operation shown in FIG. 9, the cylinder 2 with the first compartment enclosed by the first sealing stopper 8 is taken out of a drying chamber, the second compartment 9 of the cylinder 2 is filled with a diluted medicament or distilled water for injection (hereinafter referred to as "distilled water") and rapidly enclosed by the second sealing stopper 10 and cap 17 in a sterilizing chamber to prepare a finished product.

In the present invention, in order to completely enclose a medicament and distilled water in the two compartments of the cylinder by the first sealing stopper and second sealing stopper, it is preferable to design so that the diameter of the stopper is 3 to 14% larger than the inner diameter of the cylinder. The opening end 15 of the cylinder 2 is preferably tapered to be thinner toward the opening part, that is, the inner diameter of the cylinder 2 is increased, whereby insertion of the first sealing stopper and second sealing stopper into the cylinder is rendered easier.

Figure 10:
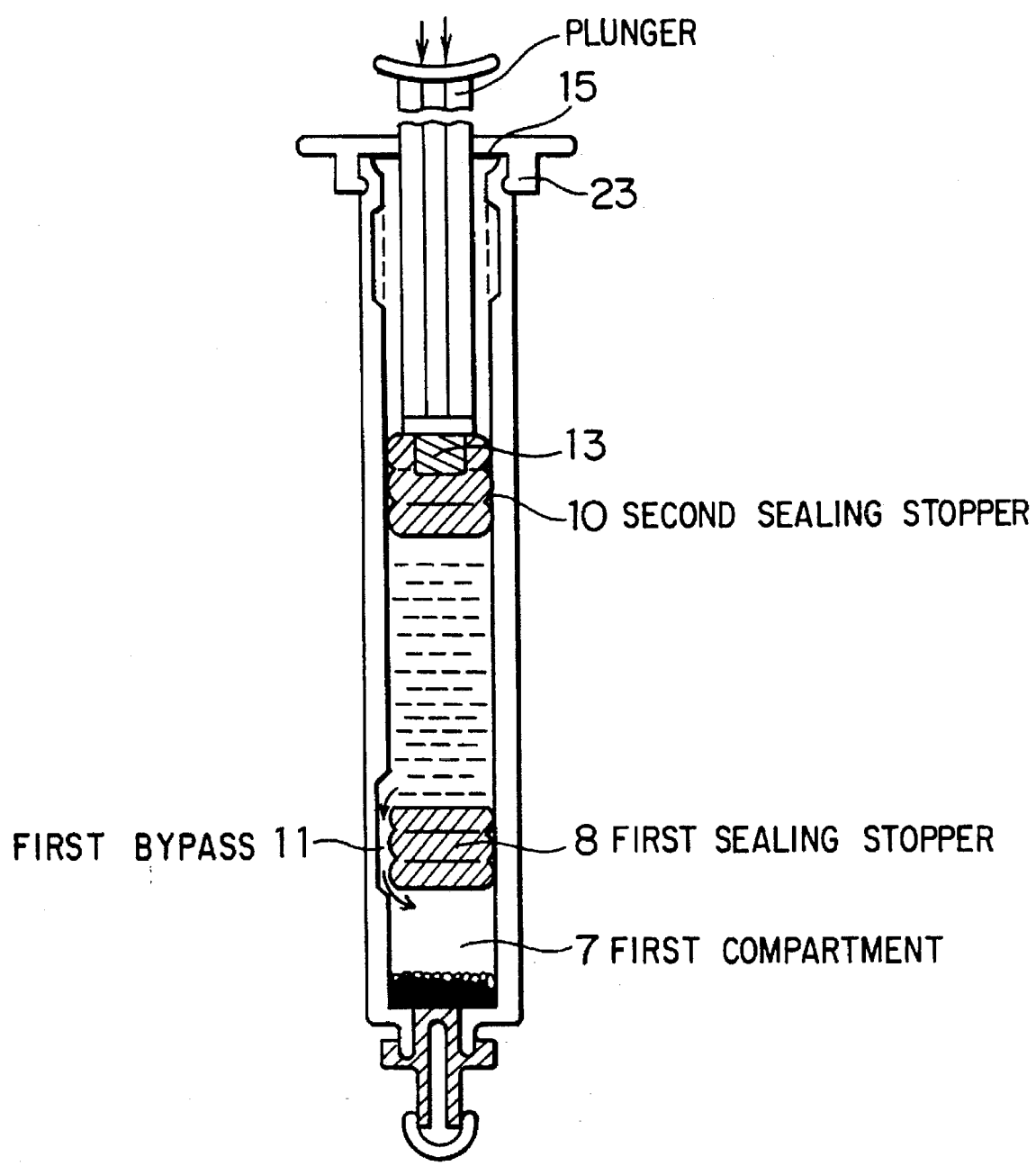
FIG. 10 is a schematic cross-sectional view showing forced adaptation of a plunger, liquid medicament and first sealing stopper in the cylinder so that the liquid medicament is passed through the bypass and flowed into the first compartment when using a syringe according to the present invention.

A method of dosing a patient with a medicament stored in the syringe-cum-container of the present invention will specifically be illustrated:

For use of a medicament filled in the syringe of the present invention as shown in FIG. 10, the cap 17 is removed from the opening part 5 of the cylinder 2 and the finger touching flange 23 as shown in FIG. 3 is inserted. When the spiral part 13 of the plunger shown in FIG. 2 is then inserted in the concave spiral part 12 of the second sealing stopper 10 and the plunger is thrust toward the front end 3 of the cylinder 2, the first sealing stopper 8 is allowed to approach the position of the first bypass 11, the distilled water is allowed to flow through the first bypass 11 and to enter the first compartment 7 and mix with a concentrated medicament or powder medicament to prepare a liquid medicament diluted to be dosed.

Figure 11:
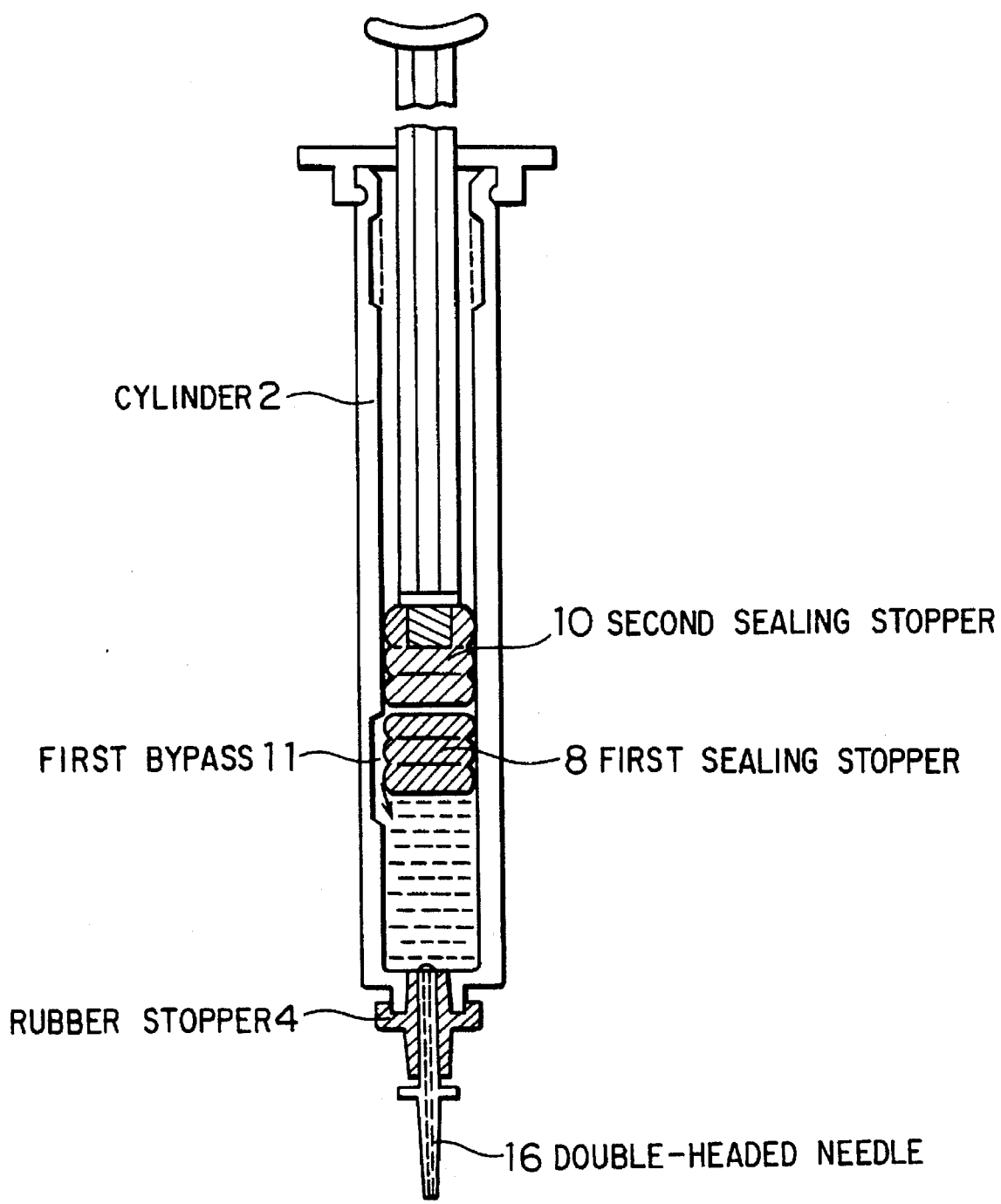
FIG. 11 is a schematic cross-sectional view showing that a double-headed needle is inserted in the syringe according to the present invention and a liquid medicament is dosed.

At this time, the double-headed needle 16 is penetrated through the rubber stopper 4 positioned at the front end 3 of the cylinder 2 as shown in FIG. 11, the air in the double-headed needle 16 is removed and the plunger is thrust in the end of the cylinder to dose a diluted medicament.

As illustrated above, the syringe-cum-container of the present invention is a syringe capable of rapidly and sanitarily preparing a liquid medicament in simple manner and then immediately dosing.

As the material of the injection cylinder used in the syringe-cum-container of the present invention, there can be used well known materials in this technical field, preferably, resins comprising, as polymeric components, cyclic olefinic compounds or bridged polycyclic hydrocarbon compounds, or resins comprising, as polymeric components, olefinic compounds. These resins can be mixed with olefinic resins and/or synthetic rubbers, or further can be mixed with at least one of other resins, for example, polyethylene, polypropylene, polyethylene terephthalate, polyethylene-vinyl alcohol, ethylene-vinyl copolymers, ethylene-vinyl acetate copolymers, nylon, amorphous nylon, ethylene-propylene copolymers, polymethylpentene and ethylene-butylene copolymers.

As the material of the first sealing stopper or second sealing stopper needing rubber elasticity, it is preferable to use synthetic rubbers having heat resistance, for example, crosslinked materials of isoprene, polybutadiene, ethylene-propylene terpolymers, isoprene-isobutylene copolymers, thermoplastic elastomers.

In addition, as the resin film for partially laminating the sealing stopper, there are preferably used, for example, fluoro resins, resins comprising, as polymeric components, cyclic olefinic compounds or bridged polycyclic hydrocarbon compounds, or resins comprising, as polymeric components, widely used olefinic compounds.

Advantages of the Invention

The syringe-cum-container of the present invention has the following benefits or advantages:

(1) In a chamber for the preparation of a medicament, a raw liquid medicament can be concentrated, dried, powdered and rapidly enclosed in a compartment of the syringe in a sanitary and economical manner by providing bypass grooves in two stages in the injection cylinder without forming protrusions on the outer circumference of the cylinder.

(2) Since the second bypass, first sealing stopper and cylinder end are designed so as to have most suitable shapes and purposefully combined in the syringe of the present invention, a thin, heat- or air-decomposable raw medicament liquid can rapidly be concentrated to prepare a stable and high-grade medicament in a simple and economical manner.

(3) The syringe of the present invention is capable of maintaining a stored medicament in a high grade for a long period of time.

What is claimed is:

1. A syringe comprising:

a cylinder having a first end and a second end, said second end being an open end;

first and second sealing stoppers slidably mounted in said cylinder, said first sealing stopper being disposed between said second sealing stopper and said first end of said cylinder, whereby a first compartment is formed between said first sealing stopper and said first end of said cylinder and a second compartment is formed between said first and second sealing stoppers;

at least one longitudinally elongated first bypass formed in an inner wall surface of said cylinder at a location intermediate said first and second ends of said cylinder, said first bypass being formed by a concave groove, and said cylinder having a smooth cylindrical shape at a location of an outer wall surface thereof corresponding to a location of said first bypass formed in said inner wall surface;

at least one longitudinally elongated second bypass formed in an inner wall surface of said cylinder at a location substantially adjacent said second end of said cylinder, said second bypass being formed by a concave groove, and said cylinder having a smooth cylindrical shape at a location of an outer wall surface thereof corresponding to a location of said second bypass formed in said inner wall surface;

wherein said second bypass has a length greater than a longitudinal thickness of said first sealing stopper; and wherein said cylinder has an uninterrupted uniform outer diameter extending from a position adjacent said first end of said cylinder to an extreme end of said second end of said cylinder.

2. A syringe as recited in claim 1, wherein said second bypass has a length of one-third to one times a longitudinal thickness of said first sealing stopper.

3. A syringe as recited in claim 1, wherein said at least one first bypass comprises a plurality of first bypasses; and said at least one second bypass comprises a plurality of second bypasses.

4. A syringe as recited in claim 1, wherein said at least one first bypass comprises a plurality of first bypasses.

5. A syringe as recited in claim 1, further comprising a removable cap fit over said open second end of said cylinder.

6. A syringe comprising:

a cylinder having a first end and a second end, said second end being an open end;

first and second sealing stoppers slidably mounted in said cylinder, said first sealing stopper being disposed between said second sealing stopper and said first end of said cylinder, whereby a first compartment is formed between said first sealing stopper and said first end of said cylinder and a second compartment is formed between said first and second sealing stoppers;

at least one longitudinally elongated first bypass formed in an inner wall surface of said cylinder at a location intermediate said first and second ends of said cylinder, said first bypass being formed by a concave groove, and said cylinder having a smooth cylindrical shape at a location of an outer wall surface thereof corresponding to a location of said first bypass formed in said inner wall surface;

a finger-engaging flange member removably fit over said open second end of said cylinder, said finger-engaging flange member having a central plunger-receiving opening formed therein;

at least one longitudinally elongated second bypass formed in an inner wall surface of said cylinder at a location substantially adjacent said second end of said cylinder, said second bypass being formed by a concave groove, and said cylinder having a smooth cylindrical shape at a location of an outer wall surface thereof corresponding to a location of said second bypass formed in said inner wall surface;

wherein said second bypass has a length greater than a longitudinal thickness of said first sealing stopper; and wherein said finger-engaging flange member has a radially inwardly projecting portion, and said cylinder has a recess in the outer wall surface thereof adjacent said second open end, said inwardly projecting portion being engageable in said recess.

7. A syringe as recited in claim 6, further comprising a removable cap fittable over said open second end of said cylinder when said finger-engaging flange member is removed.

8. A syringe as recited in claim 7, wherein said removable cap has a radially inwardly projecting portion, said inwardly projecting portion being engageable in said recess.

9. A syringe as recited in claim 6, wherein said second bypass has a length of one-third to one times a longitudinal thickness of said first sealing stopper.

10. A syringe as recited in claim 6, wherein said at least one first bypass comprises a plurality of first bypasses; and said at least one second bypass comprises a plurality of second bypasses.

11. A syringe as recited in claim 6, wherein said at least one first bypass comprises a plurality of first bypasses.

12. A syringe comprising:

a cylinder having a first end and a second end, said second end being an open end;

first and second sealing stoppers slidably mounted in said cylinder, said first sealing stopper being disposed between said second sealing stopper and said first end of said cylinder, whereby a first compartment is formed between said first sealing stopper and said first end of said cylinder and a second compartment is formed between said first and second sealing stoppers;

at least one longitudinally elongated first bypass formed in an inner wall surface of said cylinder at a location intermediate said first and second ends of said cylinder, said first bypass being formed by a concave groove, and said cylinder having a smooth cylindrical shape at a location of an outer wall surface thereof corresponding to a location of said first bypass formed in said inner wall surface;

at least one longitudinally elongated second bypass formed in an inner wall surface of said cylinder at a location substantially adjacent said second end of said cylinder, said second bypass being formed by a concave groove, and said cylinder having a smooth cylindrical shape at a location of an outer wall surface thereof corresponding to a location of said second bypass formed in said inner wall surface;

a rubber stopper fit in said first end of said cylinder, said rubber stopper having a central recess opening in a direction away from said second end of said cylinder, such that said rubber stopper has a U-shaped longitudinal cross section; and wherein said second bypass has a length greater than a longitudinal thickness of said first sealing stopper.

13. A syringe as recited in claim 12, further comprising a needle-retaining cap fit over an open end of said recess of said rubber stopper.

14. A syringe as recited in claim 13, further comprising a needle fitting tube interposed between said first end of said cylinder and said needle-retaining cap and connecting said needle-retaining cap to said first end of said cylinder.

15. A syringe as recited in claim 12, wherein said at least one first bypass comprises a plurality of first bypasses; and said at least one second bypass comprises a plurality of second bypasses.

* * * * *